(12) United States Patent
Hattori et al.

(10) Patent No.: US 6,194,468 B1
(45) Date of Patent: Feb. 27, 2001

(54) HAIR GROWTH STIMULANTS

(75) Inventors: Renzo Hattori, Tokyo; Tadashi Fukuma, Nara, both of (JP)

(73) Assignees: Takasago International Corporation, Tokyo; Seven Chemical Co., Ltd., Osaka, both of (JP)

( * ) Notice: Under 35 U.S.C. 154(b), the term of this patent shall be extended for 0 days.

(21) Appl. No.: 09/211,053

(22) Filed: Dec. 15, 1998

(30) Foreign Application Priority Data

Dec. 19, 1997 (JP) ................................................ 9-364306

(51) Int. Cl.$^7$ .................................................. A61K 31/045
(52) U.S. Cl. .......................... 514/729; 514/729; 514/880; 514/307
(58) Field of Search ..................... 514/729, 739, 514/307, 880

(56) References Cited

FOREIGN PATENT DOCUMENTS 9-143061    6/1997   (JP) ................................ A61K/9/70

OTHER PUBLICATIONS

CA 126234751, WO 9707677 Abstract, Mar. 6, 1997.*

* cited by examiner

*Primary Examiner*—Rebecca Cook
(74) *Attorney, Agent, or Firm*—Sughrue, Mion, Zinn, Macpeak & Seas, PLLC

(57) ABSTRACT

A hair growth stimulant comprising p-menthane-3,8-diol and at least one substance from the group of a blood circulation promoter, a 5α-reductase inhibitor, an antihistaminic, a cell activator, an antiphlogistic and an antimicrobial is disclosed. The hair growth stimulant is free from hormonal action, does not cause side effects and has excellent hair growth promoting effects.

6 Claims, No Drawings

HAIR GROWTH STIMULANTS

FIELD OF THE INVENTION

The present invention relates to a hair growth stimulant. More specifically, the present invention relates to a hair growth stimulant which is free from hormonal action, does not cause side effects and has excellent pilatory effects.

BACKGROUND OF THE INVENTION

As hair growth stimulants, there have been disclosed a hair growth promoting composition (JP-B-2-2852; the term "JP-B" as used herein means an "examined Japanese patent publication") comprising at least one substance selected from cinnamyl alcohol, cinnamyl alcohol esters, cinnamic acid and cinnamate compounds; and a hair growth stimulant (JP-B-3-844) which comprises 4,6,6-trimethylbicyclo (3.1.1)-hepten-3-one-2 as an active ingredient and capronium chloride, vitamin E nicotinate, benzyl nicotinate or the like used in combination as a blood circulation promoter (skin peripheral vasodepressor). It has been disclosed that since the latter one has inhibitory action against the formation of testosterone, which is a causative agent of excessive accumulation of androgen which will lead to physiological symptoms such as male pattern baldness and seborrhea, due to a reductase of 5α-dihydrotestosterone, it is able to reduce or prevent such symptoms.

It has already been reported that p-menthane-3,8-diol to be used in the present invention is a substantially odorless compound which is contained in full-grown lemon eucalyptus in a small amount (*Phytochemistry*, 23, 12, 2777(1984)).

It has been reported that p-menthane-3,8-diol heightens odor spreading and odor lasting properties (JP-A-4-337395; the term "JP-A" as used herein means an "unexamined published Japanese patent application) and it is effective as a repellent of noxious organisms (JP-B-3-80138), but there has no report on its effects of accelerating percutaneous absorption, thereby enhancing hair growth.

As a percutaneous absorption promoter containing a terpene, the following have been disclosed: a percutaneous absorption promoter (JP-A-6-48962) comprising a narcotic and/or non-narcotic analgesic and a terpene and/or an essential oil; and a percutaneous absorptive preparation for analgesic use (JP-A-9-143061), which contains, as a terpene, a hydrocarbon-based monoterpene such as limonene, a monoterpene alcohol such as 1-menthol, terpineol or borneol, a monoterpene aldehyde such as citral, a monoterpene ketone such as ionone or another monoterpene such as ceneole and/or, as an essential oil, mentha oil, peppermint oil or eucalyptus oil which is composed mainly of a terpene.

In addition, a percutaneous absorption preparation has been disclosed (JP-A-5-201879) which comprises triethylene glycol; and a terpene, for example, a monoterpene alcohol such as linalool, citronellol, geraniol, nerol, menthol, terpineol, carveol, thujyl alcohol, pinocampheol, cineole, dimethyl octanol, hydroxy citronellol, tetralinalool, muguol (produced by IFF), myrcenol or isopulegol or isomers thereof, a sesquiterpene alcohol such as farnesol, nerolidol, lanceol, santalol or vetivenol or optical or steric isomers thereof, nopol or bornyl methoxycyclohexanol and/ or an essential oil, for example, bay oil, peppermint oil, orange oil, turpentine oil, lemon oil, hops oil, basil oil, evodia fruit oil, bitter orange peel oil, sweet orange oil, pine oil, camphor oil, zanthoxylum fruit oil, coriander oil, elemi oil, gingergrass oil, eucalyptus oil, fennel oil, chenopodium oil, *Cinnamomum kanahirai* oil, fragrant olive oil, savin oil, *Chamaecyperis obtusa* oil, orange flower oil, cymbopogon georingil oil, Japanese valerian oil, sandal wood oil, myrrh essential oil, ginger oil, turmeric oil, cedar wood oil, hinoki oil, celery seed essential oil, schisandra fruit oil, clove oil, cinnamon oil, geranium oil, lavender oil, rosemary oil, pepper oil, ylang—ylang oil, Kananga oil, perilla oil, patchouli oil, vetiver oil, spearmint oil or anise oil. As a medicament to be orally administered, dantrolene sodium, ketoprofen, diclofenac sodium or flurbiprofen is also disclosed.

Various compounds and extracts of a crude drug which have been conventionally known as a hair growth composition are employed as a hair growth stimulant. As a matter of fact, however, they do not always exhibit good effects for the hair growth, because conditions of the hair vary from person to person. Even if the hair growth composition is effective to some extent, it involves defects such as difficulty in continuous use because effects of epispastic or the like. The above-described percutaneous absorptive compositions permit the exhibition of hair growth promoting effects by transferring the medicament, which has been percutaneously administered as a liquid formulation, cream or ointment, to the necessary site, but they are not satisfactory.

SUMMARY OF THE INVENTION

An object of the present invention is therefore to provide a hair growth stimulant which is free from hormonal action, does not cause side effects and has excellent hair growth promoting effects.

With a view to attaining the above object, the present inventors carried out an extensive investigation. As a result, it has been found that p-menthane-3,8-diol has the action of promoting percutaneous absorption of a skin peripheral vasodepressor or hair growth promoting agent serving as a hair growth stimulant. It has also been found that hair growth promoting effects can be improved furthermore by using in combination said p-menthane-3,8-diol and at least one substance selected from a blood circulation promoter, a 5-α-reductase inhibitor, an antihistaminic, a cell activator, an antiphlogistic and an antimicrobial. The present invention has been completed based on these findings.

The present invention concerns a hair growth stimulant comprising p-menthane-3,8-diol.

The present invention further concerns a hair growth stimulant, which comprises p-menthane-3,8-diol and at least one substance selected from the group consisting of a blood circulation promoter, a 5-α-reductase inhibitor, an antihistaminic, a cell activator, an antiphlogistic, and an antimicrobial.

DETAILED DESCRIPTION OF THE INVENTION

The present invention will hereinafter be described more specifically.

p-Menthane-3,8-diol which is a compound to be used in the present invention can be synthesized by the ring closure of commercially available citronellal with sulfuric acid [see *J. Am. Chem. Soc.*, 75, 2367(1953)]. It has isomers such as the cis-form, trans-form and optical isomers. They can be used either singly or in combination as a mixture.

p-Menthane-3,8-diol is easily soluble in a solvent for ordinarily used cosmetics, dermal compositions, hair growth stimulants or the like and can be incorporated therein freely. The amount of this substance is usually 0.01 to 20% by weight, preferably 0.1 to 15% by weight, more preferably 0.3 to 10% by weight based on the total amount of the cosmetic composition, dermal composition or hair growth stimulant as a final product. Amounts less than 0.01% do not bring about sufficient effects, while amounts exceeding 20% by weight do not bring about proportional effects.

The substance of the present invention can be incorporated as is or after being diluted with a solvent, perfume or essential oil contained therein, use of which is acceptable in the above-described cosmetic composition, dermal composition or hair growth stimulant.

Medicaments other than those with the above-described medicinal properties can be added as needed to the hair growth stimulant of the present invention. There is no particular limitation imposed on the kind of the medicament. Ordinarily-employed medicaments or coadjuvants can be used as are appropriate.

Examples of the skin peripheral vasodepressor (blood circulation promoter) or hair growth promoting agent include capronium chloride, vitamin E derivatives, cepharanthin, benzyl nicotinate, capsicum tincture, *swertiae herba* extract and *Spilanthes acmella* extract. They may be used either singly or in combination.

Examples of the 5-α-reductase inhibitor include β-glycyrrhetic acid, estradiol and estrone; and those of the antihistaminic include diphenhydramine hydrochloride. They may be used either singly or in combination.

Examples of the cell activator (hair follicular function activator) include pantothenyl alcohol, pantothenyl ethyl ether, Photosensitizer 301 and extract of ginseng; those of the antiphlogistic include glycyrrhetic acid and derivatives thereof; those of the antimicrobial include hinokitiol and isopropyl methyl phenol. They may be used either singly or in combination.

Furthermore, a humectant, amino acid, nutritional supplement, cetanol, paraffin wax, emulsifier, vaseline, beeswax, terpene alcohol such as menthol, perfume and/or coloring matter can be added as needed.

To prepare the hair growth stimulant of the present invention, various types of bases such as an emulsion, ointment, cream or lotion can be used.

The present invention will hereinafter be described more specifically by examples and tests. It should however be borne in mind that the present invention is not limited to or by the examples.

In the below-described examples, various products were prepared in accordance with the following formulation by using p-menthane-3,8-diol (product of Takasago International Corporation).

EXAMPLE 1

Hair growth stimulant formulation example 1

| | SU/JHE-S | SU/JHE-2 | SU/JHE-18 |
|---|---|---|---|
| 1. Ethyl alcohol | 1.0 | 1.0 | 1.0 |
| 2. Glycerin | 2.0 | 2.0 | 2.0 |
| 3. Polyoxyethylene sorbitan monooleate | 45.0 | 45.0 | 45.0 |
| 4. p-Menthane-3,8-diol (cis) | — | 0.5 | — |
| 5. p-Menthane-3,8-diol | — | — | 0.5 |
| 6. Cepharanthin | 0.002 | 0.002 | 0.002 |
| 7. β-Glycyrrhetic acid | 0.1 | 0.1 | 0.1 |
| 8. Benzyl nicotinate | 0.05 | 0.05 | 0.05 |
| 9. Diphenhydramine | 0.1 | 0.1 | 0.1 |

-continued

| | SU/JHE-S | SU/JHE-2 | SU/JHE-18 |
|---|---|---|---|
| hydrochloride | | | |
| 10. Perfume | trace | trace | trace |
| 11. Purified water | 51.748 | 51.248 | 51.248 |

TEST EXAMPLE 1

Method: A mouse which was at least 7 weeks old and had certainly reached telogen had its back shaved at its back into an oval shape by an electric clipper carefully so as not to hurt its skin. The mouse was then shaved at its back further by an electric shaver. From the next day after epilation, 100 μl of a test substance were applied to the shaved portion without giving a stimulus thereto by using a 200 μl chip once a day for 5 days a week. The test substance was applied for 39 days. During these days, observation was carried out daily for 5 days a week prior application. Three days after the final application, the picture of the shaved portion was taken. The area of the shaved portion and the area where regrowth was recognized were measured by a planimeter and based on them, the ratio of the restored portion was calculated. In addition, the regrown hair was shaved and its weight was measured.

Judgement: Based on the area to which the test substance was applied and the area of the restored portion which were made apparent by pictures, the ratio of the restored portion was calculated and hair regrowth was evaluated in accordance with the scoring standards.

<Scoring standards>

Hair growth

| | Hair growth | |
|---|---|---|
| Score | Range | State |
| 0 | 0 | — |
| 1 | Slight | Light gray |
| 2 | Up to ⅓ | Dark gray |
| 3 | ⅓ to ⅔ | Regrown hair, up to ⅓, |
| 4 | Almost whole | Regrown hair, up to ⅔, |
| 5 | Whole | Only regrown hair |

In this example, hair growth promoting effects of a hair growth stimulant were studied using a C3H mouse.

Su-JHE-S, which was a quasi-drug hair growth stimulant containing 0.002% by weight of cepharanthin and 0.1% by weight of β-glycyrrhetic acid, as a control, and the invention products, Su-JHE-12 and Su-JHE-18, were tested as described below.

A male 6-week-old C3H/HeN Slc mouse was employed as a test animal. After 30 mice of the above type were acclimated for one week, 24 mice free from abnormalities were selected. One group consisted of 4 mice and two groups were provided for one specimen material.

Under such testing conditions, a hair growth stimulant was externally applied to the C3H mice for 39 days. As a result, hair regrowth was found in 5 mice among 8 mice of the control Su-JHE-S group. In the Su-JEH-12 group, all of the eight mice exhibited regrowth and significant hair growth promoting effects exceeding even the scores of the area and condition concerning regrowth were recognized.

Similarly in the Su-JHE-18 group, hair regrowth was found from all the eight mice and significant hair growth promoting effects were found in the scores of the restored area and condition. The Su-JHE-18 group was superior to the Su-JHE-12 group particularly in the score of the area. Table 1 shows the results of the score concerning regrowth, while Table 2 shows the results of a weight change.

TABLE 1

Score concerning regrowth

|  | Su-JHE-S | Su-JHE-12 | Su-JHE-18 |
|---|---|---|---|
| Number of mice whose hair showed regrowth | 5/8 | 8/8 | 8/8 |
| Weight of regrown hair (mg) | 15.825 ± 9.946 | 23.737 ± 7.103 | 36.088 ± 14.083* |
| Score of area | 1.625 ± 0.680 | 3.250 ± 0.366** | 3.625 ± 0.375*** |
| Score of condition | 2.125 ± 0.693 | 3.750 ± 0.250** | 3.750 ± 0.412** |

(Numeral: average ± S.E.,
*significant at 90%,
**significant at 95%,
***significant at 99%)

TABLE 2

Weight change

|  | Su-JHE-S | Su-JHE-12 | Su-JHE-18 |
|---|---|---|---|
| Before administration | 23.29 ± 0.311 | 23.75 ± 0.453 | 22.63 ± 0.375 |
| Week 1 | 24.50 ± 0.423 | 25.25 ± 0.491 | 25.00 ± 0.463 |
| Week 2 | 25.38 ± 0.263 | 25.88 ± 0.611 | 25.75 ± 0.559 |
| Week 3 | 26.25 ± 0.250 | 26.50 ± 0.707 | 26.75 ± 0.648 |
| Week 4 | 26.75 ± 0.313 | 27.00 ± 0.707 | 26.88 ± 0.549 |
| Week 5 | 27.38 ± 0.263 | 27.88 ± 0.718 | 27.75 ± 0.620 |
| Day of judgment | 27.63 ± 0.493 | 28.25 ± 0.701 | 27.63 ± 0.625 |

EXAMPLE 2

Hair growth stimulant formulation example 2
1. Ethyl alcohol 60.0%
2. *Swertiae herba* extract 2.0
3. Ginger tincture 1.0
4. Benzyl nicotinate 0.05
5. p-Menthane-3,8-diol 0.3
6. Propylene glycol 2.0
7. Polyoxyethylene hydrogenated castor oil 0.5
8. Perfume trace
9. Purified water 34.15

Preparation process: The above ingredients 2 to 8 were dissolved in the ingredient 1, followed by the addition of the ingredient 9, whereby a hair growth stimulant was prepared.

EXAMPLE 3

Hair growth stimulant formulation example 3
1. Ethyl alcohol 50.0
2. Hinokitiol 0.2
3. dl-α-Tocopherol acetate 0.5
4. Pantothenyl ethyl ether 1.0
5. Estradiol 0.02
6. p-Menthane-3,8-diol 1.0
7. Polyoxyethylene polyoxypropylene cetyl ether 0.3
8. 1,3-butylene glycol 1.5
9. Perfume trace
10. Purified water 45.48

Preparation process: The above ingredients 2 to 9 were dissolved in the ingredient 1, followed by the addition of the ingredient 10, whereby a hair growth stimulant was prepared.

EXAMPLE 4

Hair cream formulation example
1. Liquid paraffin 18.0%
2. Paraffin wax 2.0
3. White petrolatum 10.0
4. White beeswax 2.0
5. Butyl paraben 0.1
6. Self-emulsifying type glycerin monostearate 1.0
7. Polyoxyethylene hydrogenated castor oil 3.0
8. dl-α-Tocopherol acetate 0.5
9. Purified water 56.45
10. Carboxyvinyl polymer 0.15
11. 1,3-butylene glycol 4.0
12. Disodium edetate 0.1
13. Methyl paraben 0.1
14. Borax 0.1
15. Perfume trace
16. *Swertiae herba* extract 1.0
17. Benzyl nicotinate 0.05
18. Hinokitiol 0.5
19. p-Menthane-3,8-diol 3.0

Preparation Process: The above ingredients 1 to 8 were dissolved under heat and kept at 80° C. To the resulting solution, a solution which had been prepared by gradually adding the purified water 9 to the ingredients 10 to 14 and dissolving the latter in the former under heat and then had been kept at 82° C. in advance, was added under stirring to mix them. The resulting mixture was then cooled under stirring, followed by the addition of the above ingredients 15 to 19, which had been dissolved at 50° C. Stirring was continued until the temperature lowered to 35° C., whereby a hair cream was prepared.

EXAMPLE 5

Ointment formulation example
1. p-Menthane-3,8-diol 2.0
2. Isopropyl myristate 10.0
3. Cetanol 2.0
4. Paraffin wax 6.0
5. Microcrystalline wax 10.0
6. Emulsifier 11.0
7. Purified water 59.0

Preparation process: The above ingredients 1 to 6 were melted under heating to 80° C. to form a uniform mixture, followed by the addition of the ingredient 7 which had been heated separately. Intermittent stirring was continued until the resulting mixture was cooled and solidified.

The incorporation of p-menthane-3,8-diol in a hair growth stimulant according to the present invention makes it possible to increase the percutaneous absorption, thereby accelerating hair growth promotion. The hair growth promoting effects can be improved more by the use of at least one substance selected from a blood circulation promoter, a 5α-reductase inhibitor, an antihistaminic, a cell activator, an antiphlogistic and an antimicrobial in combination with p-menthane-3,8-diol which promotes the percutaneous absorption of a skin peripheral vasodepressor or hair growth promoting agent serving as a hair growth stimulant.

While the invention has been described in detail and with reference to specific embodiments thereof, it will be apparent to one skilled in the art that various changes and modifications can be made therein without departing from the spirit and scope thereof.

What is claimed is:

1. A hair growth stimulant composition comprising p-methane-3,8-diol in an amount effective to increase percutaneous absorption, and at least one blood circulation promoter in amount effective to stimulate hair growth.

2. The hair growth stimulant composition according to claim 1, wherein the blood circulation promoter is at least one substance selected from the group consisting of capronium chloride, a vitamin E derivative, cepharanthin, benzyl nicotinate, capsicum tincture, *swertiae herba* extract and *Spilanthes acmella* extract.

3. The hair growth stimulant composition according to claim 2, wherein the blood circulation promoter is at least one substance selected from the group consisting of a vitamin E derivative, cepharanthin, benzyl nicotinate and *swertiae herba* extract.

4. A hair growth stimulant composition comprising p-methane-3,8-diol in an amount effective to increase percutaneous absorption, at least one blood circulation promoter in an amount effective to stimulate hair growth and at least one substance selected from the group consisting of a 5-α-reductase inhibitor, an antihistaminic, a cell activator, an antiphlogistic and an antimicrobial.

5. The hair growth stimulant composition according to claim 4, wherein the 5-α-reductase inhibitor is at least one substance selected from the group consisting of β-glycyrrhetic acid, estradiol and estrone; the antihistaminic is diphenhydramine hydrochloride; the cell activator is at least one substance selected from pantothenyl alcohol, pantothenyl ethyl ether; the antiphlogistic is glycyrrhetic acid or a derivative thereof; and the antimicrobial is one substance selected from hinokitiol or isopropyl methyl phenol.

6. A method for stimulating hair growth comprising applying to a host in need of said hair growth composition comprising a blood circulation promoter and a substance selected from the group consisting of 5-α-reductase inhibitor, an antihistamine, a cell activator, an antiphlogistic and an antimicrobial, each in an amount effective to stimulate hair growth and p-menthane-3,8-diol in an amount effective to increase absorption of said blood circulation promoter and substance.

* * * * *